United States Patent [19]

Waters et al.

[11] Patent Number: 4,632,902

[45] Date of Patent: Dec. 30, 1986

[54] METHOD FOR DETECTING BIOLOGICAL ACTIVITY IN A BODY FLUID

[75] Inventors: John R. Waters, Towson; Rodney Broman, Fallston, both of Md.

[73] Assignee: Becton, Dickinson and Company, Franklin Lakes, N.J.

[21] Appl. No.: 688,276

[22] Filed: Jan. 3, 1985

Related U.S. Application Data

[63] Continuation-in-part of Ser. No. 527,144, Aug. 29, 1983, abandoned, which is a continuation of Ser. No. 294,857, Aug. 20, 1981, abandoned.

[51] Int. Cl.$^4$ ............................................. C12Q 1/02
[52] U.S. Cl. ..................................... 435/29; 435/803; 210/679
[58] Field of Search .................... 210/679; 435/29, 31, 435/32, 33, 34, 36, 37, 38, 253, 254, 255, 803, 261, 245, 244

[56] References Cited

U.S. PATENT DOCUMENTS 4,174,277 11/1979 Melnick et al. ..................... 210/679

OTHER PUBLICATIONS

Frobisher (1970) Fundamentals of Microbiology 8th Edition. W. B. Saunders Co. Philadelphia pp. 266–268.

*Primary Examiner*—Sam Rosen
*Assistant Examiner*—William J. Herald
*Attorney, Agent, or Firm*—James R. McBride

[57] ABSTRACT

A method of detections biological activity is disclosed. A nutrient growth medium which isolates antibiotics and other microbial growth inhibitors during culturing of a microorganism. The growth medium includes an aqueous dispersion of nutrient materials and an effective amount of an isolating substance or substances capable of isolating antimicrobial materials during culturing of a microorganism. The isolating substances are selected from ion exchange resins and non-functional adsorbent resins.

12 Claims, No Drawings

METHOD FOR DETECTING BIOLOGICAL ACTIVITY IN A BODY FLUID

The present application is a continuation-in-part of U.S. patent application Ser. No. 527,144, filed Aug. 29, 1983 which is a continuation of U.S. patent application Ser. No. 294,857, filed Aug. 20, 1981 now both abandoned.

The present invention is directed generally to an improved means for the detection of biological activity in a body fluid sample containing an antibiotic or other antimicrobial inhibitor. More particularly, the present invention is directed to an improved microbial growth medium containing an effective amount of a substance capable of isolating antimicrobial inhibitors.

BACKGROUND OF THE INVENTION

Biological activity in blood, such as bacteremia (bacteria in blood), remains a significant problem despite the availability of antimicrobial drugs. In particular, the rapid isolation of offending organisms from bacteremic patients is made more difficult when the patient has been administered antibiotics, which are transferred along with the bacteria in the blood into culture broths and often inhibit the growth of the organism. It is nevertheless important that the identification and susceptibility of an infecting organism to various antimicrobial drugs be determined as early as possible in the course of bacteremia.

When conventional culturing techniques are employed to identify an infecting organism, the administration of an antibiotic prior to drawing the blood sample for testing can result in inhibition of the growth of bacteria, thus interfering with isolation and identification of the bacteria. Even when antibiotics may not be present in the blood, the isolation of the offending organism(s) still may require excess periods of incubation because of inhibitors contained in serum, plasma, or lysed erythrocytes.

Similar problems exist despite the type of body fluid being examined, whether it is urine, spinal fluid, abscess exudates, serum, pertioneal fluid and the like.

Antibiotics inhibit bacteria through a variety of mechanisms. One of these mechanisms is to inhibit the bacteria's ability to synthesize its cell wall. Inhibition of cell wall synthesis is caused by antibiotics belonging to the $\beta$-lactam or cephalosporin groups. This includes such examples as penicillin G, amipicillin, amoxicillin, carbenicillin, nafcillin, ticarcillin, cefamandole, cefotaxime, cefoxitin, cephalexin, cephaloridine, cephalothin and moxalactam.

A primary function of the bacterial cell wall is to allow the cell to live in a fluid environment which is less dense than the interior of the cell. Because the bacterium's cytoplasm (interior) is much more dense than the fluid surrounding the cell, there is a large osmotic pressure difference. This causes water to be drawn into the bacterium and were it not for its rigid cell wall, the cell would swell and burst. When synthesis of the cell wall is inhibited by antibiotics, the cell wall is weakened and osmotic pressure can cause lysis (bursting) and death of the bacteria.

Weakening of the bacterium's cell wall by an antibiotic does not take place instantaneously, but usually over a period of hours. The time required is affected by several factors including the concentration of antibiotics and the rate of growth of the bacterium. If a patient has a bacterial infection of the blood and is being treated with a -lactam or cephalosporin class antibiotic, there is a probability that at a given time during treatment there is a population of bacteria in the blood which has been weakened, but not killed by the antibiotic. A sample of this patient's blood when added to normal blood culture medium may show no viable bacteria to be present, for cell wall damaged bacteria in the blood may lyse due to osmotic stress in the culture medium. This would be a false negative result.

Adding a carbohydrate saccharide, such as sucrose (for example) to a culture medium increases its density and such media are described as hypertonic. In hypertonic media, there is less of a difference in density between the bacterium's cytoplasm and the surrounding fluid. This causes less of an osmotic differential and therefore less osmotic stress on the bacterial cell. Cell wall-damaged bacteria can thus survive more easily in hypertonic media.

The usual method for detection of bacteria is to inoculate 5 ml of a body fluid into a culture medium and wait for the appearance or turbidity which is an indication of bacterial growth. Patients who have been subjected to antibiotic therapy will have the antibiotic present in the body fluid at the time the fermentation is initiated. Presence of the antibiotic inhibits growth of the bacteria and may delay isolation of the bacteria for as long as 14 days.

More recently, a radiometric technique for the detection of biological activity in the blood has undergone clinical testing and has been adopted for commercial practice. In that method, samples of blood are inoculated into a suitable growth medium that includes a $C^{14}$ containing carbon source, the inoculated medium is incubated for a suitable period, and a portion of the gaseous atmosphere is analyzed for $C^{14}O_2$ while in the gaseous state. Such process is described, inter alia, in U.S. Pat. No. 3,676,679 issued July 11, 1972; and in the articles "Early Detection of Bacterial Growth, with Carbon[14] Labeled Glucose," Radiology, 92, No. 1, pp. 154–5 (January 1969); "Automated Radiometric Detection of Bacterial Growth in Blood Culture," J. Labs. Clin. Med., 75, No. 3, pp. 529–34 (March 1970); and "Automated Radiometric Detection of Bacteria in 2,967 Blood Cultures," Applied Microbiology, 22, No. 5, pp. 846–849 (November 1979). A commercial instrument for the practice of a rapid, automated process is available under the trademark BACTEC (Johnston Laboratories). Although this method can be used to rapidly determine the presence of bacteria in a culture in the absence of antibiotics or their inhibitors, it is inefficient when growth is attempted in the presence of antibiotics or other inhibitors in the culture media.

Antibiotics can be separated from microorganisms by membrane chromatography, but these procedures are not practical because of the complexity of the separation technique and the high rate of contamination of the test culture.

U.S. Pat. No. 4,174,277 to Melnick et al. discloses a method for separation of antibiotics from microorganisms present in a body fluid sample. In the method of the Melnick patent, an antibiotic is selectively removed from a bacterially infected body fluid specimen by adsorbing the antibiotic onto a resin system treated with a detergent.

The detergent renders the resin system selective for the antibiotic while permitting the bacteria to remain free in the eluting fluid and thus the bacteria are separated from the antibiotic. The eluted body fluid specimen containing the bacteria is then inoculated into a growth medium and cultured.

While the method of the Melnick et al. patent has been useful in overcoming the problem of antibiotic inhibitor contamination of blood samples, it introduces a separate handling step in the treatment of body fluid samples prior to the conventional culturing process. The separate handling step is particularly cumbersome and may introduce contamination when handling a multitude of samples as is done with current automatic fermentation apparatus.

It is therefore, a principal object of the present invention to provide a culture medium for the growth and detection of an infecting organism in a body fluid specimen without the need to resort to a separate step for separation of an antibiotic or inhibiting substance.

It is another object of this invention to provide a means for isolating antimicrobial inhibitors from body fluid specimens during growth of an organism in culture medium.

It is a further object of the present invention to provide a means for isolating antibiotics from an infected body fluid specimen without significantly affecting the metabolism of the microorganism population of the specimen during growth in culture medium.

It is yet another object of the present invention to provide a method utilizing a resin which will isolate antibiotics and other inhibitors contained in a body fluid specimen while exhibiting little effect on growth of microorganisms in the specimen.

It is still another object of the present invention to provide a resin for isolating materials inhibitory to microorganisms in a body fluid specimen without affecting the microbial population of the specimen.

SUMMARY OF THE INVENTION

This invention relates to a culture medium for growth of microorganisms containing an effective amount of a substance capable of isolating antimicrobial materials in an infected body fluid specimen. The isolating substances of the invention are ion exchange resins and nonionic adsorbent resins, characterized by their capacity for isolation of antibiotics and other inhibitors. The isolating substances may be used with any conventional growth media, such as commercially available anaerobic, aerobic and hypertonic growth media.

Although ion exchange resins and adsorbent resins are known to adsorb charged antibiotics from fluid specimens, they have not proven to be a satisfactory means for removing antibiotics from bacterially infected specimens where rapid isolation and identification of an infecting bacterium is the objective. The reason attributed to this lack of success in the use of ion exchange resins and adsorbent resins for treatment of antibiotic containing specimens is that upon passage of a specimen containing an antibiotic and an infecting organism through a resin, the resultant filtrate is not only substantially freed of the antibiotic, but the infecting bacteria are also significantly removed by the resin.

For the foregoing reasons many research efforts have been directed to modifying ion exchange resins and/or nonionic adsorbent resins to provide a resin capable of removing the antibiotic or other inhibitor without removal of the infecting bacteria from the body fluid sample. U.S. Pat. No. 4,174,277 to Melnick et al. is exemplary of these efforts to modify resins for selective removal of antibiotics and other bacterial inhibitors from the body fluid sample.

Because of the effectiveness of ionic exchange resins and nonionic adsorbent resins for removal of infecting microoganisms, as well as nutrients and antibiotics, from a culture medium, it has been thought by the industry to be impossible to isolate antibiotics and other inhibitors from the nutrient broth without, at the same time, isolating the microorganism and the nutrients contained in the culture medium including a body fluid sample.

In accordance with the present invention, it has now been discovered that ion exchange resins and nonionic adsorbent resins can be present in a culture medium during culturing of a body fluid sample without interference with the ability of the infecting microorganism to grow in the culture medium while at the same time effectively isolating the antibiotic or other inhibitor from interference with microorganism growth. Rapid culturing and analysis of the microorganism in the specimen are thereby made possible without a separation step to remove antibiotics and other inhibitors. The resins do not require any modification, such as those described in U.S. Pat. No. 4,174,277 to Melnick et al., prior to use in the present invention. The resins can be used in any type of growth medium, including hypertonic growth media which afford osmotic protection to bacterial cells which have been damaged by the presence of an antibiotic. The hypertonic media permit such damaged bacteria to survive and grow.

DETAILED DESCRIPTION OF THE INVENTION

In accordance with the present invention a substance capable of isolating an antimicrobial is added to a culture medium to provide a stabilized culture medium. The stabilized culture medium can then be used to culture a body fluid specimen infected with a microorganism and contaminated with an antibiotic or other antimicrobial while isolating the antimicrobic from interfering with growth of the microorganism contained in the specimen.

The substances which may be employed in the present invention to isolate antimicrobics in culture media are resins or combinations of resins which are known to adsorb antimicrobics. It is to be understood that throughout this application the adsorption by the resins of the invention refers to the ability of the resins to isolate microorganism growth inhibitors without interference with microorganism growth. The physical effect of the resins on other materials which may be present in the culture medium, including the infecting microorganism, is not significant so long as the microorganism growth inhibitor is isolated from interference with microorganism growth.

More particularly, the resins which may be used in the practice of the present invention include ion exchange resins and non-functional polymeric resin adsorbents. The resins which may be employed in the practice of the invention include synthetic ion exchange resins and non-functional nonionic adsorbent resins with matrices formed from condensation and addition polymers. Specifically, polystyrene resins cross-liked with divinyl benzene may be used.

The resins do not require any modifications, such as the surfactant treatment of the Melnick et al. patent, prior to use. Resins suitable for use in the present invention which have been treated by surfactant in accordance with the Melnick et al. patent remain suitable for use in the present invention. That is, surfactant treatment of the resin does not alter, in any material degree, the ability of the resins to isolate antimicrobics in accordance with the invention while still permitting growth of microorganisms.

Sodium, hydrogen and ammonium charged cation exchange resins have been found to be particularly suitable for use in the present invention. The following cation exchange resins have been found to be effective:
BIO REX
AG 50W—$X_2, X_4, X_6, X_8, X_{10}, X_{12}$, and $X_{16}$ from BIO-RAD Laboraotories,
DOWEX
50W—$X_2, X_4, X_8, X_{10}, X_{12}$, and $X_{16}$
from Dow Chemical Company and Rexyn 101 from Fisher Scientific Co., all of which are strong acid polystyrene resins having $SO_3^-$ functional group. The cation exchange resins are particularly useful in combination with the non-functional resins, such as the XAD resins manufactured by Rohm & Haas and SM resins sold by BioRad.

Chloride, formate, acetate and hydroxide, charged anion exchange resins have generally been found to be suitable. Specifically, chloride charged anionic exchange resins in combination with adsorbent resins sold under the following trademarks have been found effective in the practice of the invention. DOWEX 1-X8 from Dow Chemical Company, DUOLITE A-109 from Diamond Shamrock Company and AMBERLITE IRA400 from Rohm & Haas, all of which are strong base resins having polystyrene quaternary amonium functional groups; DUOLITE A-7 from Diamond Shamrock Company and AMBERLITE IR45 from Rohm & Haas, which are weakly basic and have tertiary amine functional groups. The anion exchange resins are preferably used in combination with a non-functional resin such as the XAD resins from Rohm & Haas and SM resin from BioRad, particularly XAD-4 resin which is a nonfunctional copolymer of styrene and divinyl benzene.

It should be understood that the pore size of the resin is not critical or important in the practice of the present invention. Generally, resins do not have a pore size sufficient to permit bacteria to penetrate into the interior of the resin. Certain resins, however, have macroporous structures with large internal surfaces which permit large molecules to penetrate their interiors. Such macroporous resins are entirely suitable for use in the practice of the present invention since entrapment of the bacteria within the pores does not necessarily limit growth of the bacteria in the presence of the culture medium. Resins which have relatively smaller pores wherein adsorption is affected principally on the external surfaces of the resin, that is, microporous resins are also suitable in the practice of the invention. A particularly preferred combination is a non-functional polymeric adsorbent resin, such as XAD-4 and a cationic exchange resin. Such a combination resin isolates antibiotics as well as other bacterial inhibitors, while not interfering significantly with the growth of microorganisms contained in a body fluid specimen.

In general, it is preferred to use from about 0.5 to about 5 grams (dry weight basis) of a non-functional polymer adsorbent resin in combination with from about 0.05 to about 1.0 grams (dry weight basis) of an ion exchange resin for each 30 ml of microbial growth media. At the above indicated levels of resin, the growth medium is suitable for culturing up to about 10 ml of body fluid specimen, preferably from about 2 ml to about 5 ml of body fluid specimen.

The resins of the invention will isolate antimicrobials and other inhibitors from infected body fluid specimens including urine, blood, spinal fluid and the like. Generally, the body fluid specimen is transferred aseptically to a vial containing the resins and a suitable culture medium by perforating the septum of the vial with the syringe needle and injecting a sample of the body fluid specimen into the vial. The vial is placed on a shaker or other suitable device and shaken for a sufficient time to allow contact of the resin and the specimen. Any other type of apparatus or method which provides sufficient contact between the resin and the specimen to assure contact of the antibiotic or other antimicrobic with the resin may also be employed.

After shaking, tumbling or otherwise contacting the specimen with the resin, the vial containing the resin, the culture medium and the specimens is maintained under suitable incubation conditions to permit fermentation of the microorganisms in the specimen. Shaking may continue during the culturing process.

Generally, for use in a radiometric assay, the process employs a nutrient culture medium that contains water, a suitable $C^{14}$ containing carbon source, a nitrogen source minerals and trace elements. Typical $C^{14}$ containing carbon sources may be glucose, fructose, galactose, mannose, rhamnose, or the like, phenylalanine, lysine, arginine or the like, glycerol, urea, or carboxylic acids such as citric acid or the like. Generally, the levels of radioactivity will vary from about 0.1 to about 10 microcuries per 10 ml. The assimilable nitrogen source may be either organic or inorganic, such as nitrates, nitrites, ammonia, urea, amino acids, or the like, while minerals such as the chlorides, sulfates or phosphates of calcium, sodium, potassium, magnesium or the like of trace elements such as magnesium or the like, manganese, iron, zinc, cobalt or the like, may also be employed. Vitamins, cofactors or other enrichment agents such as anticoagulants may also be added if desired. Finally, the medium may also include a buffer for pH adjustment and maintenance. The atmosphere above the culture medium can be air, oxygen, or the like if aerobic tests are being conducted, whereas nitrogen, $CO_2$, or the like can be employed if anaerobic tests are being conducted.

A broad selection of possible components that may be included in the media is also set out in U.S. Pat. No. 3,676,679. While that patent indicates that up to 20 percent or more carbohydrate may be employed in the medium, preferred media contain up to about 0.5 percent carbohydrate and commercial media do contain such small amounts of carbohydrate added as such. In addition, if the media contains peptone, yeast extract, or the like, an additional 1 percent or so of carbohydrates may be present as a component of this additive.

As indicated, the resins of the present invention are useful in hypertonic media. A hypertonic medium is a medium which has an osmolarity greater than a sample specimen which is added to the medium. Osmolarity is defined as the molarity of an ideal solution of a non-dissociating substance that exerts the same osmotic pressure as the solution being considered. The commonly used osmolarity range for hypertonic media is from about 500 to about 1000 milliosmoles per liter. Any suitable osmotic agent can be used to provide a hypertonic media. U.S. Pat. No. 4,206,282 to Hochstein describes a variety of suitable osmotic agents including sucrose, sorbitol, mannitol and erythritol.

Vials containing media for aerobic cultures, designated No. 6, and vials containing media for anaerobfc cultures, designated No. 7, are commercially available from Johnston Laboratories. The vials are of 50 ml nominal capacity and contain 30 ml of culture medium and have a radioactivity of about 2 microcuries. A medium suitable for aerobic fermentation (6) may contain tryptic soy broth, hemin, menadione, sodiumpolyanethol sulfonate, and $C^{14}$-labelled substrates, while a medium suitable fvor anaerobic culture (7) may contain tryptic soy broth, yeast extract, hemin, menadione, L-cysteine, sodium-polyanethol sulfonate and $C^{14}$-labelled substrates. The 50 ml vials contain 30 ml of medium and have a radioactivity of about 2 microcuries. Commercial media have a pH of about 7.3

Where a specimen to be analyzed contains a known and identified antibiotic, a resin which is known to be effective to isolate that antibiotic is selected and added to the culture media containing the body fluid specimen. Where a specimen contains one or more unidentified antibiotics, a combination of resins which will isolate various antibiotics and permit growth of the microorganisms is used. The specimen is contacted with the selected resins in accordance with the above-described methods during fermentation.

The following examples further illustrate various features of the invention but are not intended to any way limit the scope of the invention which is defined in the appended claims.

EXAMPLE 1

To determine whether resins had an effect on the ability of a medium to support growth, blood specimens were prepared by adding a particular microorganism at a level of 100 colony forming units (CFU) or less to 5 ml whole blood samples. The inoculated blood specimens were added to 50 ml vials containing either 30 ml of a culture medium or 30 ml of a culture medium containing 4 grams of XAD-4 nonionic polymeric resin adsorbent (Rohm & Haas) and 0.25 grams of a cationic exchange resin, sodium form, such as Rexyn 101 resin (Fisher Scientific). The culture medium, designated 6B, has the following formulation:

| LIST OF INGREDIENTS | AMOUNT | |
|---|---|---|
| Purified Water | 30 | ml |
| Tryptic Soy Broth | 2.75% | W/V |
| Hemin | 0.0005% | W/V |
| Vitamin K | 0.00005% | W/V |
| $^{14}$C—Labeled Substrates | 2.0 | Ci |
| Sodium Bicarbonate | 0.0375% | W/V |
| $CO_2$ Atmosphere | 10% | VV |
| Sucrose | 0.25% | W/V |
| Pyridoxal HCL (Vitamin $B_6$) | 0.001% | W/V |
| Sodium polyanetholsulfonate | 0.025% | W/V |

The separate vials containing blood specimens inoculated with particular microorganisms were placed in a reciprocating shaker and incubated for 24 hours at 37° C. Samples containing the particular microorganisms were grown in separate vials containing the culture medium and were also grown in separate vials containing the culture medium with the above described resins. The results of the growth comparisons are set forth hereinbelow in Table 1 (+ means that growth was detected).

TABLE 1
GROWTH IN CULTURE MEDIUM WITH RESINS

| | 6B | 6B + Resins |
|---|---|---|
| S. aureus | + | + |
| E. coli | + | + |
| GpD Streptococcus | + | + |
| N. meningitidis | + | + |
| N. gonorrheae | + | + |
| P. aeruginosa | + | + |
| P. alcaligenes | + | + |
| P. testosterosis | + | + |
| S. bovis | + | + |
| Streptococcus | + | + |
| Moraxella sp | + | + |
| S. morbillorium | + | + |
| S. pneumoniae | + | + |
| P. acne | + | + |
| K. pneumoniae | + | + |
| H. influenzae | + | + |
| Candida albicans | + | + |
| Torulopsis glabrata | + | + |

Thereafter, the 5 ml blood specimen and various organisms were inoculated into the culture media followed by addition of antibiotics as set forth hereinbelow in Table 2. Again, dual samples were fermented, one of the samples containing only the 6B culture medium and the other sample containing the 6B culture medium plus the above described resin. In each case, as shown hereinbelow in Table 2, the culture medium with the resin provided positive growth even in the presence of the antimicrobics.

TABLE 2
PROTECTIVE EFFECT OF RESINS

| Organism | Drug (Conc/Vial) | Growth 6B | 6B + Resin |
|---|---|---|---|
| S. aureus | Penicillin G (0) | + | + |
| | Penicillin G (100 units) | − | + |
| | Amikacin (0) | + | + |
| | Amikacin (200 µg) | − | + |
| | Erythromycin (0) | + | + |
| | Erythromycin (250 µg) | − | + |
| | Methicillin (0) | + | + |
| | Methicillin (250 µg) | − | + |
| P. aeruginosa | Amikacin (0) | + | + |
| | Amikacin (200 µg) | − | + |
| | Gentamicin (0) | + | + |
| | Gentamicin (140 µg) | + | + |
| E. coli | Gentamicin (0) | + | + |
| | Gentamicin (140 µg) | − | + |
| Candida albicans | Amphotericin B (0) | + | + |
| | Amphotericin B (100 µg) | − | + |
| S. aureus | Gentamicin (0) and Ampicillin (0) | + | + |
| | Gentamicin (140 µg) and Ampicillin (250 µg) | − | + |

Two different organisms (Staphylococcus aureus and a Group A Streptococcus) were treated with penicillin G to cause damage to their cell walls. The penicillin G treatment was found to have killed many of the organisms but leave many others damaged, or stressed, as desired. These stressed organisms were then added to various blood culture media to determine which of the media allowed better recovery of the damaged bacteria. The medium bottles also contained penicillin G to cause further stress to the bacteria. The culture media designated 6B, 8B and 18B have the following formulations:

| List of Ingredients | Amount | | | |
|---|---|---|---|---|
| | 6B | 16B | 8B | 18B |
| Purified Water | 30 ml | 30 ml | 30 ml | 30 ml |
| Tryptic Soy Broth | 2.75% wv | 2.75% wv | 2.75 wv | 2.75% wv |
| Hemin | 0.0005% wv | 0.0005% wv | 0.00% wv | 0.0005% wv |
| Vitamin K | 0.00005% wv | 0.00005% wv | 0.0005% wv | 0.00005% |
| "C—Labeled Substrates | 2.0 Ci | 2.0 uli | 2.0 Ci | 2.0 uli |
| Sodium Bicarbonate | 0.0375% wv | 0.0375% wv | 0.035% wv | 0.0375% wv |
| CO2 Atmosphere | 10% wv | 10% wv | 10% wv | 10% wv |
| Sucrose | 0.25% wv | 0.25% wv | 10% wv | 10% wv |
| Pyridoxal HCl (vitamin B6) | 0.001% wv | 0.001% wv | 0.001% wv | 0.001% wv |
| SPS (see Note 1) | 0.025% wv | 0.025% wv | 0.025% wv | 0.025% wv |
| Antifoaming Agent | 0.01% wv | — | 0.01 vv | — |
| Non-Ionic Absorbing Resin | — | 13.3% wv | — | 13.3% wv |
| Cationic Exchange Resin | — | 0.8% | — | 0.8% wv |

The table below summarizes results of multiple experiments testing the recovery in resin medium (16B) and hypertonic resin medium (18B). The values presented are the number of cultures where growth occurred (positive cultures) during a seven day test period.

| | *Staphylococcus aureus* | | Group A Streptococcus | |
|---|---|---|---|---|
| Treatment | Resin Medium (16B) | Hypertonic Resin Medium (18B) | Resin Medium (16B) | Hypertonic Resin Medium (18B) |
| None (control) | 12 | 12 | 6 | 6 |
| Penicillin Stress | 66 | 120 | 15 | 27 |

These results show that organisms which are not stressed or damaged grow equally well in the two media, while penicillin damaged bacteria grow significantly better in the medium containing sucrose (hypertonic). The hypertonic resin medium allowed growth in 81% more cases (average for both organisms) than did the isotonic resin medium. In order to more closely simulate clinical conditions, these experiments were repeated with four ml of human blood added to the media. Similar results were obtained.

In other experiments, penicillin-stressed organisms were tested under similar conditions in media which did not contain resins (normal medium-6B, and hypertonic medium-8B). The cell wall-damaged bacteria rarely grew in the normal media and grew only slightly better in the hypertonic media. These results show that when antimicrobials are present in the culture medium, sucrose alone is not sufficient to allow good recovery of the stressed bacteria. Resins must also be present. Results of these experiments are summarized below:
1. The penicillin treatment caused stress (damage) to the test organisms.
2. These stressed organisms grew in hypertonic resin medium in 81% more cases than in resin medium which was not hypertonic.
3. Similar results were obtained when human blood was present in the culture media.
4. Hypertonic medium without resin did not substitute for the hypertonic medium with resin.
5. Media which were neither hypertonic nor contained resin rarely supported growth of penicillin stressed bacteria.

It is concluded from these experiments that growth of cell wall-damaged bacteria in a culture medium which contains an antibiotic is significantly better when the medium is both hypertonic and contains resins. Many patients who are being tested for septicemia (organisms present in their blood) are being treated with antimicrobials. Their blood samples may therefore contain the antimicrobial agents (hence the need for resins to neutralize them), and bacteria whose cell walls have been damaged by the antimicrobials (which calls for a hypertonic medium for their protection).

EXAMPLE 3

An experiment was conducted which tested for any effect of Triton X-100 treatment of the two resins used in Example 2 on either organism growth or drug neutralization. Both resins (white and black beads) were treated with 0.10%, 0.05% and 0.01% of a detergent (Triton X-100) in accordance with the method disclosed in U.S. Pat. No. 4,174,277. These treated resins, and non-treated control resins, were used to make 16B medium for the tests having the formulation set forth in Example 2.

Four organisms, *Neisseria meningitidis, Staphylococcus aureus, Pseudomonas aeruginosa* and a Group A Streptococcus were inoculated into the above test media at a concentration of approximately $10^2$ cfu per bottle and growth observed over the following five days. Results are shown below:

| | TOTAL GI VALUES | | | |
|---|---|---|---|---|
| | Triton X-100 Treatment | | | |
| | None | 0.10% | 0.05% | 0.01% |
| *N. meningitidis* | 393 | 375 | 345 | 329 |
| *S. aureus* | 1658 | 1672 | 1651 | 1606 |
| *P. aeruginosa* | 1162 | 1185 | 1146 | 1165 |
| Group A. Strep. | 392 | 431 | 405 | 395 |

All organisms under all four test conditions became positive at the same time (17 hours after inoculation). These results show that treatment of the resins with a detergent has no significant effect on the growth and detection of representative microorganisms in accordance with the method of this invention.

In another experiment, the effect of Triton X-100 treatment of the resins on the ability of 16B medium to neutralize an antimicrobial was tested. The Trtion X-100 treatment was the same as described above. Gentamicin was present at 140 μg/bottle. An additional bottle of medium without resins was included (6B medium) as a control. Results are seen below:

|  | Time to Detection (Hours) | | | | |
|---|---|---|---|---|---|
|  | 6B No Resin | Triton Treatment | | | |
|  |  | None | 0.10% | 0.05% | 0.01% |
| S. aureus | NG* | 17 | 17 | 17 | 17 |
| P. aeruginosa | NG | 17 | 17 | 17 | 17 |
| Group A. Strep. | NG | 23 | 23 | 23 | 23 |

*No growth over five days

These data show that resin neutralization of the antimicrobial was not affected by the presence or absence of Triton X-100 treatment.

What is claimed is:

1. A method for detecting biological activity in a body fluid sample which may contain antimicrobial material wherein:
   (a) a growth medium is inoculated with a body fluid sample
   (b) the inoculated growth is cultured under conditions conducive to the occurrence of normal metabolic processes for a period of time sufficient to cause production of metabolic byproducts, and
   (c) the metabolic byproducts are monitored to detect biological activity,
   (d) the improvement comprising incorporating into said growth medium an effective amount of a resin capable of isolating any antimicrobial material present in said body fluid sample without hindering biological activity during said culturing period.

2. The method of claim 1 wherein said resin is an ion exchange resin.

3. The method of claim 1 wherein said resin is a non-functional resin adsorbent.

4. The method of claim 1 wherein said resin is a non-functional resin adsorbent in combination with an ion exchange resin.

5. The method of claim 2 or 4 wherein said ion exchange resin is a cationic exchange resin.

6. The method of claim 5 wherein the cationic exchange resin is in the sodium form.

7. The method of claim 1 wherein the resin is selected from the group consisting of a non-functional copolymer of divinyl benzene and styrene, an ion exchange resin which is a copolymer of divinyl benzene and styrene and combinations thereof.

8. The method of claim 1 wherein the body fluid sample is blood.

9. The method of claim 1 wherein the body fluid sample is urine.

10. The method of claim 1 wherein the body fluid sample is spinal fluid.

11. The method of claim 1 wherein the body fluid sample is peritoneal fluid.

12. The method of claim 1 wherein said resin is detergent coated.

* * * * *